US011957327B2

(12) United States Patent
García Vitoria et al.

(10) Patent No.: US 11,957,327 B2
(45) Date of Patent: Apr. 16, 2024

(54) DURAL SEALING SYSTEM

(71) Applicants: FUNDACIÓN PARA EL FOMENTO DE LA INVESTIGACIÓN SANITARIA Y BIOMÉDICA DE LA COMUNITAT VALENCIANA, Valencia (ES); INSTITUTO DE BIOMECÁNICA DE VALENCIA, Valencia (ES)

(72) Inventors: Carles García Vitoria, Valencia (ES); Carlos Manuel Atienza Vicente, Valencia (ES); Fernando Mollà Doménech, Valencia (ES); Víctor Javier Primo Capella, Valencia (ES)

(73) Assignees: FUNDACIÓN PARA EL FOMENTO DE LA INVESTIGACIÓN SANITARIA Y BIOMÉDICA DE LA COMUNITAT VALENCIANA, Valencia (ES); INSTITUTO DE BIOMECÁNICA DE VALENCIA;, Valencia (ES)

(*) Notice: Subject to any disclaimer, the term of this patent is extended or adjusted under 35 U.S.C. 154(b) by 77 days.

(21) Appl. No.: 16/606,259

(22) PCT Filed: Apr. 19, 2018

(86) PCT No.: PCT/ES2018/070313
§ 371 (c)(1),
(2) Date: Oct. 18, 2019

(87) PCT Pub. No.: WO2018/193144
PCT Pub. Date: Oct. 25, 2018

(65) Prior Publication Data
US 2020/0054312 A1 Feb. 20, 2020

(30) Foreign Application Priority Data
Apr. 19, 2017 (ES) ................ ES201730626

(51) Int. Cl.
A61B 17/00 (2006.01)
A61B 17/06 (2006.01)
(Continued)

(52) U.S. Cl.
CPC .... *A61B 17/0057* (2013.01); *A61B 17/00491* (2013.01); *A61B 17/06166* (2013.01);
(Continued)

(58) Field of Classification Search
CPC ...... A61B 17/0057; A61B 2017/00575; A61B 2017/00579; A61B 2017/00584;
(Continued)

(56) References Cited

U.S. PATENT DOCUMENTS 5,053,046 A * 10/1991 Janese ................ A61B 17/3401
606/215
5,061,244 A * 10/1991 Yurkewych ........ A61B 17/3401
604/117
(Continued)

OTHER PUBLICATIONS

Nozzle Definition & Meaning, Merriam-Webster, https://www.merriam-webster.com/dictionary/nozzle, accessed Dec. 31, 2022, copyright 2022 Merriam-Webster, Incorporated (Year: 2022).*
(Continued)

*Primary Examiner* — Kankindi Rwego
(74) *Attorney, Agent, or Firm* — Casimir Jones, SC; Tristan A. Fuierer

(57) ABSTRACT

The present invention refers to a dural sealing system (100) comprising an implant (10), joined to a guiding thread (20); a transfer device (30), provided with a grip portion (30a) and a hollow portion (30b), said hollow portion (30b) terminating, at a first end, in a nozzle (30c) that can be coupled to an epidural needle (200), said hollow portion (30b) also terminating in a second end fitted with an entry region (30d); and an introductory device (70) comprising a tube (70a) with a
(Continued)

hollow interior section, provided with a first free end and a second closed end, attached to a stop (70b).

15 Claims, 5 Drawing Sheets

(51) Int. Cl.
  *A61B 17/34* (2006.01)
  *A61L 31/12* (2006.01)
  *A61M 5/32* (2006.01)

(52) U.S. Cl.
  CPC ........ *A61B 17/3401* (2013.01); *A61L 31/129* (2013.01); *A61M 5/3293* (2013.01); *A61B 2017/00004* (2013.01); *A61B 2017/00659* (2013.01); *A61B 2017/06176* (2013.01)

(58) Field of Classification Search
  CPC ........... A61B 2017/00588; A61B 2017/00592; A61B 2017/00597; A61B 17/06166; A61B 2017/06176; A61B 17/0401; A61B 2017/0403; A61B 2017/0404; A61B 2017/0406; A61B 17/00491; A61B 2017/00004; A61B 2017/00659; A61B 17/3401; A61B 17/06; A61B 17/06109; A61L 31/129; A61M 5/3293; A61M 5/46; A61M 5/30; A61M 5/31501; A61M 25/0014; A61M 2025/0007; A61M 2205/00; A61M 2205/3331; A61M 2205/3344
  USPC ......................... 606/213, 214, 216, 229, 230
  See application file for complete search history.

(56) References Cited

U.S. PATENT DOCUMENTS

| | | | | |
|---|---|---|---|---|
| 5,480,389 | A * | 1/1996 | McWha | A61B 17/3401 604/165.02 |
| 5,649,959 | A * | 7/1997 | Hannam | A61B 17/0057 606/213 |
| 5,725,504 | A * | 3/1998 | Collins | A61B 17/3401 604/117 |
| 5,836,916 | A * | 11/1998 | Corn | A61B 17/3401 604/158 |
| 6,162,192 | A * | 12/2000 | Cragg | A61B 17/0057 604/15 |
| 6,346,084 | B1 * | 2/2002 | Schnell | A61M 1/3641 600/561 |
| 9,226,738 | B2 | 1/2016 | Defonzo et al. | |
| 2003/0135237 | A1 * | 7/2003 | Cragg | A61B 17/0057 606/213 |
| 2003/0144695 | A1 | 7/2003 | McGuckin et al. | |
| 2005/0234509 | A1 * | 10/2005 | Widomski | A61B 17/0057 606/213 |
| 2006/0276840 | A1 | 7/2006 | Perper et al. | |
| 2008/0139950 | A1 * | 6/2008 | Molnar | A61B 5/022 600/499 |
| 2010/0211000 | A1 | 8/2010 | Killion et al. | |
| 2012/0116447 | A1 | 5/2012 | Stanley et al. | |
| 2013/0226227 | A1 | 8/2013 | Terwey | |
| 2014/0236223 | A1 * | 8/2014 | Porter | A61B 17/0057 606/213 |
| 2017/0007220 | A1 | 1/2017 | White | |

OTHER PUBLICATIONS

International Search Report, dated Aug. 21, 2018.
Supplemental European Search Report for European Patent Application No. 18788442, dated Dec. 7, 2020.

* cited by examiner

DURAL SEALING SYSTEM

CROSS-REFERENCE TO RELATED APPLICATIONS

This application is filed under the provisions of 35 U.S.C. § 371 and claims the priority of International Patent Application No. PCT/ES2018/070313, filed on 19 Apr. 2018 entitled "DURAL SEALING SYSTEM" in the name of Carles GARCÍA VITORIA, et al., which claims priority to Spanish Patent Application No. P201730626 filed on 19 Apr. 2017, both of which are hereby incorporated by reference herein in their entirety.

FIELD OF THE INVENTION

The present invention belongs to the technical field of implants and medical instruments.

More particularly, the device of the invention refers to a system intended for sealing the dura mater of a patient previously subjected to a medical procedure in their epidural region which involved the puncture or perforation of the dura mater.

STATE OF THE ART

The human spinal cord is bathed in cerebrospinal fluid (CSF), which, in turn, is contained within the complex known as the dural sac: this is made up of the meninges, the outer-most section of which is the dura mater. The epidural space surrounds the dural sac and is a space adjacent and exterior to the dura mater. It is occupied by connective tissue, epidural fat, and veins.

In a number of medical procedures it is necessary to access, through the use of needles, the human epidural space. This is the case, for example, injection at this site of local anaesthetics or corticosteroids for the treatment of chronic pain, or for the placement of a catheter that allows infusion of anaesthetics; this modality is used in surgery of the lower limbs, and, very frequently, in analgesia for labour in childbirth.

Usually, it is the intention of the doctor to situate the tip of the needle (and the catheter, if it is going to pass therethrough) within the epidural space, without piercing the dura mater. On occasion, however, this layer, whose thickness is around 0.3 millimetres, is unintentionally pierced and the interior of the dural sac is accessed: this causes the cerebrospinal fluid (CSF) which is housed in the sac to escape through the needle. The loss of pressure in the medullar channel due to this leakage of fluid causes a clinical condition known as post-dural puncture headache (PDPH).

Sealing of this perforation can avoid the occurrence of the PDPH clinical condition by minimising the flow of CSF lost through the needle (which, if the leak is not sealed, continues to leak from the dural sac once the needle is removed).

In addition, on other occasions, intentional punctures of the dura mater are made to extract CSF or to insert anaesthetic into the CSF. In this type of medical procedures, it is also necessary to avoid the appearance of the PDPH clinical condition.

Therefore, there is the need to develop dural sealing devices that permit completion of the dural sealing process as quickly as possible.

In the state of the art, various devices have been conceived for sealing the dura mater once said medical procedures have taken place, without the necessity to previously remove said epidural needle. However, said state-of-the-art sealing devices are mere prototypes and, apparently, have not yet been placed on the market.

In the United States patent application no. 2006/0276840, a device is disclosed for treating dural punctures that comprises an implant in the form of a patch of collagen-type material attached, through a neck portion, to a strand of suture. According to this invention, the epidural needle employed to carry out said intervention, is not removed immediately after having concluded the medical intervention. On the contrary, it takes advantage of the fact that the distal end is still lodged in the dural sac of the patient and the patch is manually introduced into the lumen (or inner hole) of said epidural needle, with the help of a catheter of smaller diameter than the lumen of the epidural needle. For this, the patch is first placed on the distal end of the catheter and the thread is made to pass through the lumen of the catheter. Afterwards, the physician responsible for the dural sealing grasps the catheter by its opposite end, called the proximal end, and slides it inside the lumen of the epidural needle until the patch reaches the distal end of the epidural needle lodged in the interior of the dural sac. Finally, the epidural needle is removed, and the patch is pulled toward the dura mater, by manually pulling the thread, to seal the orifice or perforation created as a consequence of the medical intervention.

The operations of dural sealing that may be performed with devices according to the patent application no. 2006/0276840 will be technically complicated. In addition, the success thereof will depend, to a large extent, on the physician having plenty of expertise and a steady hand, given that the necessary operations, such as the introduction of the patch through the lumen of the epidural needle, are carried out in a completely manual fashion without the help of any other device except the aforementioned catheter.

Therefore, there is the need to develop dural sealing devices that simplify the sealing process and increase the effectiveness thereof.

Furthermore, there is a potential risk that the patch, despite having been correctly positioned over the orifice or perforation of the dura mater, may be able to migrate distally toward the interior of the dural sac, coming into contact with the CSF and travelling either towards the caudal part or towards the brain. This can pose a neurological risk, in addition to preventing the correct sealing of the dural lesion.

In view of the above, it is also desirable to develop dural sealing devices that reduce the probabilities that the implant suffers a distal migration.

DEFINITIONS

Throughout this descriptive specification, it must be understood that the term "proximal" refers to that portion of an element or device that—once mounted on the dural sealing system according to the present invention—is closest to the physician in charge of carrying out the dural sealing. On the other hand, the term "distal" refers to that portion of an element or device that—once mounted on the dural sealing system according to the present invention—is closest to the patient.

Also, it should be understood that the "longitudinal" direction corresponds to the main direction of the epidural needle when it has not yet been removed from the patient.

Finally, for the purposes of the present invention a "biocompatible material" is a pharmacologically inert material designed to be implanted or incorporated into a human or animal, which does not produce an immune response or rejection in the recipient. Likewise, a "bioreabsorbable material" is a pharmacologically inert material that, once implanted or incorporated into a human or animal, is capable of being absorbed without producing an immune response or rejection in the recipient.

PURPOSE OF THE INVENTION

To address the problems and disadvantages existing in the state of the art, the invention provides a dural sealing system comprising:

An implant joined to a guiding thread of diameter D1;

A transfer device provided with a grip portion and a portion of hollow longitudinal section of diameter D2, said hollow portion terminating, at a first end, in a nozzle that can be coupled to an epidural needle of internal diameter D3, said hollow portion also terminating in a second end provided with an entry region; and An introductory device comprising a tube of diameter D5, less than D3, the tube having an interior hollow section of diameter D4, greater than D1, and being provided with a first free end and a second end attached to a stop.

The transfer device of the dural sealing system, according to the present invention, is attached by means of the nozzle to the proximal end of the epidural needle after the dural puncture, whether voluntary or accidental, has occurred, and always before removing the needle from the puncture site. The nozzle is preferably provided with a threaded connection for attaching to the epidural needle, most preferably a Luer-type threaded connection.

Before attaching the nozzle to the epidural needle, both the implant joined to the thread as well as the introductory device, have been previously mounted on the transfer device so that they are ready to be transferred through the interior of the epidural needle for their final application over the dural puncture. For this, in a first step, the free end of the introductory device is introduced into the transfer device through the entry region until said end protrudes through the nozzle tip. In a second step, the thread to which the implant is joined, is installed inside the introductory device through the free end of the hollow tube, so that the implant is placed in the distal portion of said tube and the thread extends coaxially along the hollow longitudinal section of the tube. Once this step has been carried out, the resulting assembly, i.e., the introductory device with the implant situated in the distal portion of the tube and the thread extending coaxially to the hollow interior section of the tube, are jointly introduced into the transfer device in a proximal direction through the nozzle so that the implant is positioned longitudinally inside the distal tip of said nozzle.

The placement of the implant in the distal portion of the tube of the introductory device and the thread in the hollow section of said tube, as well as the insertion of the resulting assembly in the transfer device through the nozzle (described in the preceding paragraph) occurs, preferably, at the manufacturing stage of the dural sealing system according to the invention. This simplifies the process of dural sealing by reducing the number of steps required to complete it and also reduces its execution time.

Once the assembly formed by the introductory device, the implant and the thread have been introduced into the transfer device (as described in the preceding two paragraphs), and the transfer device has been connected through the nozzle to the proximal end of the epidural needle, the physician grasps the grip portion of the transfer device, while gently pushing the tube with their finger or with the help of the stop on the introductory device, so that the assembly formed by the introductory device, the implant, and the thread passes through the nozzle, accessing the lumen of the epidural needle.

Subsequently, the assembly formed by the introductory device, the implant, and the thread continues being pushed until the implant and the thread exit from the tip of the epidural needle lodged in the dural sac. Next, the epidural needle and the introductory tube are removed slowly so that the implant is deployed in the dural sac, as it is no longer confined inside the lumen of the epidural needle. Finally, the thread is carefully pulled to place the implant on the inner face of the dura mater, called the arachnoid mater.

In a preferred embodiment of the invention, the tube of the introductory device is provided with a first mark, the transfer device is provided with a second mark, and said first and second marks coincide spatially in that position in which the introductory device protrudes from the tip of the epidural needle.

In this way, the physician can know exactly when the implant has reached the dural sac in order to proceed with the removal of the epidural needle and introductory tube, and to place the implant on the arachnoid mater.

The transfer device of the system according to the invention, serves, therefore, as a guide to the assembly (formed by the introductory device, the implant, and the thread), facilitating adequate alignment of the assembly with the lumen of the epidural needle and its correct introduction in said lumen. It also allows the physician in charge of the dural sealing to have greater accuracy when moving it through the inside of the needle, as well as when removing the introductory device and the epidural needle.

Furthermore, the transfer device according to the present invention, allows the physician to introduce the assembly formed by the introductory device, the implant, and the thread into the lumen of the epidural needle using only one hand. In this way, their other hand remains free to hold the epidural needle and the risk that lesions caused by unintentional movement of the epidural needle may appear, for example, in the spinal cord, is reduced.

In a preferred embodiment of the invention, the length of the tube of the introductory device is equal to or slightly greater (1-2 mm) than the sum of the lengths of the epidural needle and the portion of hollow longitudinal section of the transfer device. In this way, it is ensured that said tube cannot protrude from the tip of the epidural needle, invading the dural sac, any more than is necessary in order for the implant to leave the inside of the epidural needle and be able to be deployed.

In another preferred embodiment of the invention, the transfer device is provided with a block that comes into contact with the stop of the introductory tube as soon as the implant has gone through the lumen of the epidural needle and has accessed the dural sac. In this way, said introductory tube is impeded from continuing to advance and invade said dural sac.

In a preferred embodiment of the invention, the transfer device is also provided with some means of blocking the introductory device, which is intended to secure the introductory device in a specific position.

The blocking means allows better control of the position of the assembly formed by the introductory device, the implant, and the thread during its displacement along the lumen of the epidural needle. Furthermore, in the case in which said assembly is placed in the transfer device during the manufacturing process, it also avoids possible unwanted displacement before use.

In another preferred embodiment of the invention, the transfer device also comprises a conduit for the administration of surgical sealant connected to the portion of hollow longitudinal section. The system of the invention also preferably comprises a surgical sealant administration device connected to the conduit for the administration of surgical sealant.

Said surgical sealant administration device preferably comprises some means of administration by pressure that allows the surgical sealant to go through the conduit for the administration of surgical sealant and the hollow longitudinal portion of the transfer device until it accesses the lumen of the epidural needle, reaching the guiding thread and, more preferably, reaching the implant. The means of administration by pressure can optionally be a syringe.

When the surgical sealant reaches the guiding thread, this forms a mechanical block that hinders the migration of the implant towards the inside of the dural sac. Furthermore, if the surgical sealant reaches the implant, it will contribute to an improvement in the sealing of the dura mater by closing possible gaps existing between the implant and the perforation of the dura mater.

The surgical sealant can be any glue used routinely in medical applications, for example, an absorbable glue, a biological sealant or a synthetic sealant, preferably an absorbable synthetic sealant. More preferably, the surgical sealant comprises a solution of polyethylene glycol ester (PEG) and a solution of trilysine amine. Yet more preferably, the surgical sealant is DuraSeal® (trade name).

The implant of the dural sealing system according to the present invention, is preferably manufactured from a biocompatible and bioreabsorbable material of synthetic or natural origin. More preferably, it is made of bioreabsorbable polymer of polycaprolactone (PCL), polylactic acid (PLA), or combinations thereof.

According to table 1, the mechanical properties of both materials are the following:

TABLE 1

|  | PCL | PLA |
| --- | --- | --- |
| Bending resistance | 15.85-31.24 MPa | 80 MPa |
| Young's Modulus | 336-579 MPa | 3.5 GPa |

PCL is a material that is more elastic than PLA, which has more resistant mechanical properties. In view of this, and depending on the specific technical requirements that a particular application may require, it may be decided to employ one material or the other, and even a combination of both.

The implant for use in the present invention preferably has the shape of an elongated sheet with preferably rounded ends, provided with a hole in its central portion to attach the guiding thread. It is preferred that the implant has this shape because in this way it avoids the implant having to rest on the dura mater to rotate it, pulling the guiding thread and placing it in the working position (i.e., sealing the dura mater perforation).

Most preferably, the implant has the shape of an elongated sheet with rounded ends, provided with a hole in its central portion to secure the guiding thread, and having the following dimensions: 3-6 mm in length, 0.5-1 mm in width, 0.2 to 0.4 mm in thickness, and a hole of 0.2 to 0.4 mm in diameter.

The guiding thread for use in the present invention is preferably made of a biocompatible and bioreabsorbable material of synthetic or natural origin, for example and without limiting character, surgical suture thread. Furthermore, the guiding thread for use in the present invention is preferably provided with a widened portion that makes a stop, which prevents the implant from exiting.

The guiding thread for use in the present invention has an approximate diameter of preferably between 0.1 mm and 0.35 mm equivalent to a gauge of between 2/0 and 5/0. More preferably, the gauge of thread to be used in the present invention will be 4/0.

Examples of surgical suture thread for use in the present invention are: Safil Quick®, Movosyn® Mono Plus® marketed by the B. Braun company.

The guiding thread for use in the present invention it is, yet more preferably, barbed suture thread, with barbs arranged against the grain. That is to say, the barbs are arranged so that they do not exert resistance when the assembly formed by the introductory device, the implant and the thread, is displaced through the lumen of the epidural needle, from the transfer device, toward the tip of the epidural needle. However, they do resist any movement in the opposite direction.

The barbs present on threads of this type provide additional mechanical attachment that reduces the possibility of migration of the implant.

PREFERRED EMBODIMENTS OF THE INVENTION

In the following a number of concrete examples of the invention are described—without limiting character—with reference to the attached figures. In said figures, the components with the same or similar functions have been designated using the same reference number.

Figure 1:
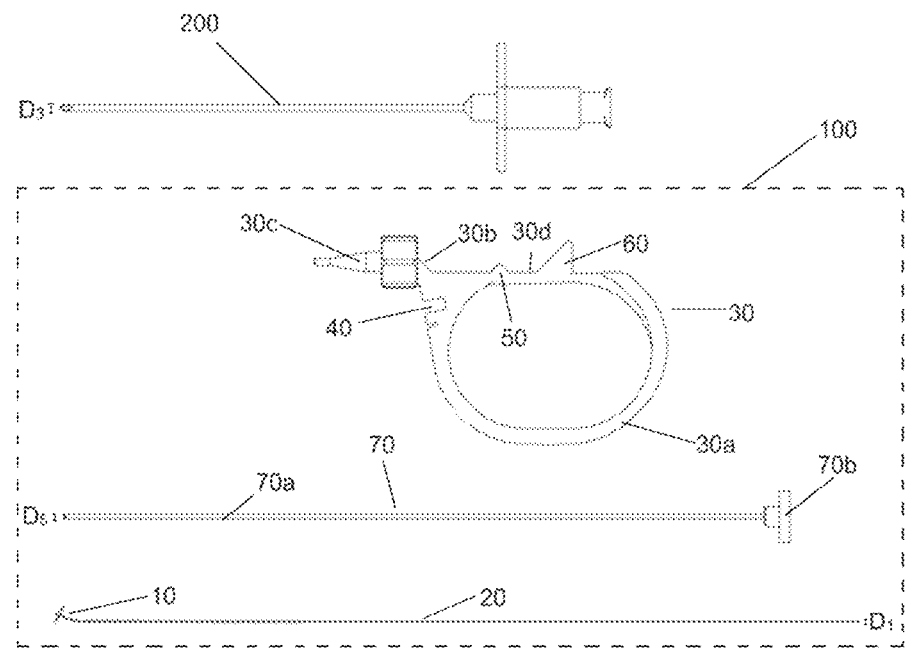
FIG. 1 shows the various elements that comprise a first embodiment of the dural sealing assembly according to the invention in schematic form.
Figure 2:
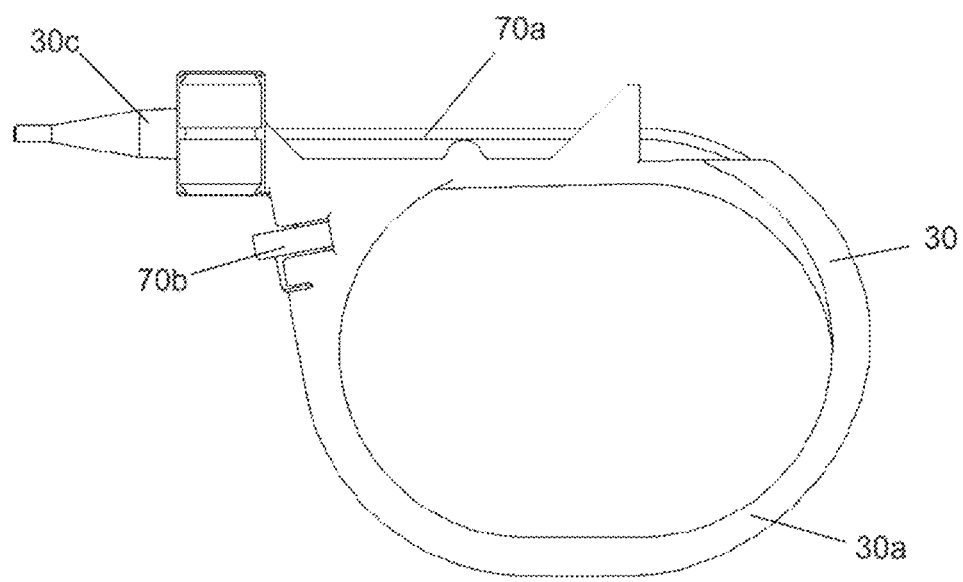
FIG. 2 shows a side view of the dural sealing assembly of FIG. 1 with all its elements mounted.
Figure 3:
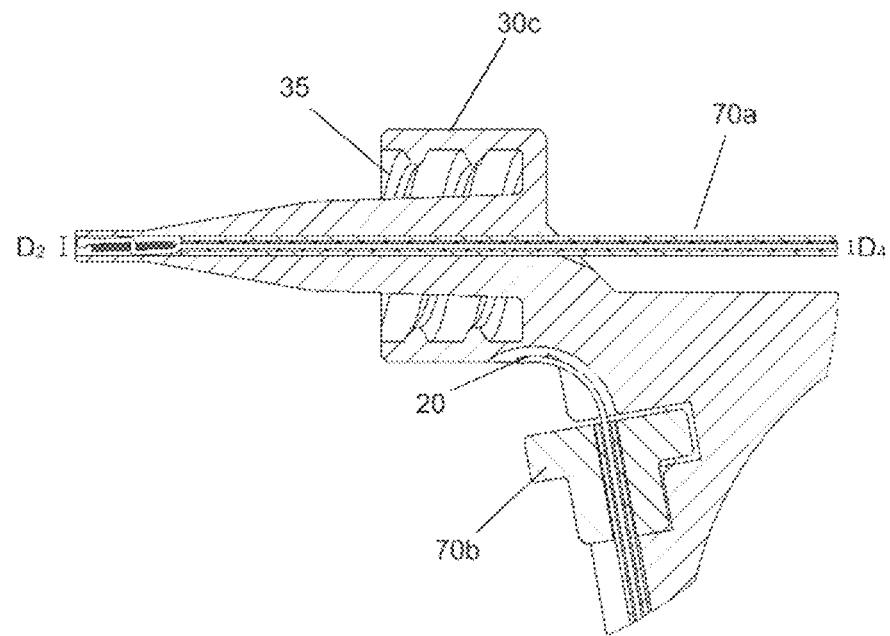
FIG. 3 is a cross-section view of the dural sealing assembly shown in FIG. 2.

In FIGS. 1 to 3 a dural sealing assembly 100, according to a first embodiment of the invention, is shown comprising an implant 10 joined to a guiding thread 20 of section D1 (4/0 gauge, approximately 0.15-0.2 mm). In the case of a barbed guiding thread 20, the diameter could be 0.4 mm counting the dimensions of the barbs or spicules.

The implant 10 has the shape of an elongated sheet with rounded ends, provided with a hole in its central portion to attach the guiding thread 20. The dimensions of the implant 10 are, in this embodiment and without limiting character: 3.5 mm in length, 0.8 mm in width, 0.35 mm in thickness, and the central hole has a diameter of 0.3 mm.

The transfer device 30, comprises a portion 30a of a ring-shaped grip and a portion 30b of hollow section and diameter D2. The portion 30b of hollow section terminates, at one of its ends, the distal end, in a nozzle 30c, intended to connect with an epidural needle 200 with an inside diameter D3 (in this embodiment, it is an epidural needle of gauge 18 G, with an approximate internal diameter of 0.85 mm). The other end of the portion 30b, the proximal end, is the entry region 30d.

The dural sealing assembly 100 shown in FIGS. 1 to 3 can also be used with epidural needles 200 of gauge 17 G of a diameter greater than 0.85 mm.

The introductory device 70 comprises, in this embodiment of the invention, a hollow tube 70a. In this embodiment of the invention, the tube 70a has a length of approximately 157 mm and a diameter D5 of approximately 0.8 mm. The tube 70a is provided with a hollow inner section of diameter D4, capable of housing the guiding thread 20 inside it (in this embodiment, approximately 0.45 mm), and terminates in a first free end, and a stop 70b attached to its second end.

In this embodiment of the dural sealing assembly 100 of the invention, the introduction of the introductory device 70, the implant 10, and the thread 20 into the entry region 30d of the transfer device 30 occurs during the manufacturing process.

The transfer device 30 is advantageously provided with a notch 40 intended to accommodate the stop 70b, as shown in FIG. 2, to avoid possible unwanted movements of the introductory device 70 before starting the operation of dural sealing.

Furthermore, the transfer device 30 is advantageously provided with a guiding projection 50, intended to facilitate the movement of the tube 70a when it is introduced through the lumen of the epidural needle 200, during the operation of the dural sealing. In order to prevent the tube 70a entering the dural sac, the transfer device 30 is provided with a block 60, arranged at the proximal end of the hollow portion 30b at the end of the entry region 30d, which prevents the stop 70b from passing a specific longitudinal position of the transfer device 30.

FIG. 3 is a cross-section view of the nozzle 30c of the transfer device 30, in which it can be seen how the implant 10 is placed according to the longitudinal direction, parallel to the guiding thread 20. This form of placement occurs during the manufacturing process and facilitates the movement of the implant 10 along the epidural needle 200 and its subsequent placement over the perforation of the dura mater.

In said FIG. 3, the internal diameters D2 (of the hollow section of the transfer device 30) and D4 (of the tube 70a) are also graphically shown, and it can furthermore be seen how the nozzle 30c is provided with a thread 35 for attaching to the epidural needle.

Figure 4:
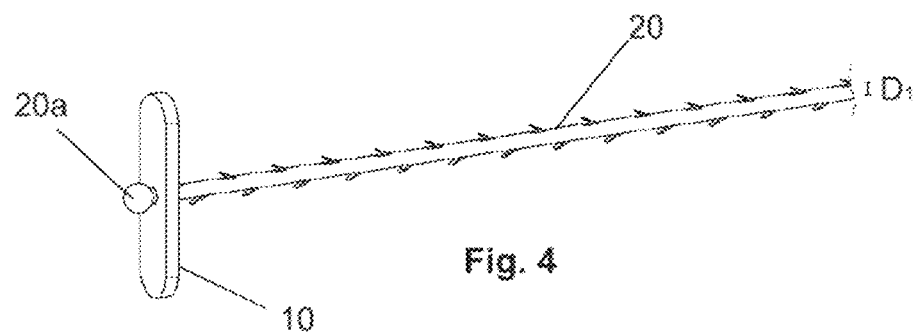
FIG. 4 shows a possible embodiment of the implant and the barbed guiding thread according to the present invention.

FIG. 4 shows an embodiment of the invention in which the guiding thread 20 is a barbed surgical suture provided with a widened portion 20a that acts as a stop and avoids that the thread detaches from the implant 10.

FIGS. 5a-5d show the procedure of using the assembly 100 of the invention, during an operation of dural sealing.

Figure 5A:
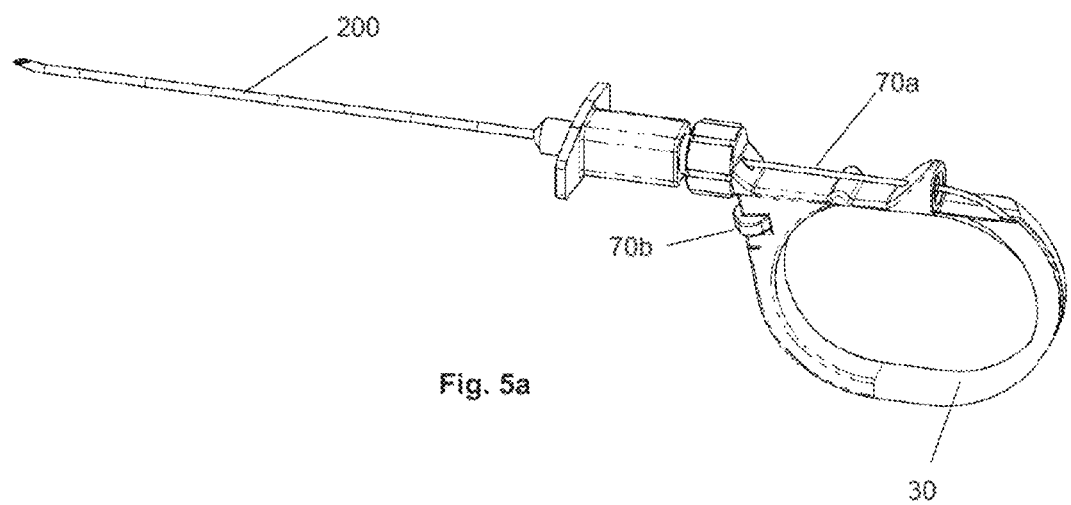
FIG. 5a illustrates the introduction of the introductory device 70, the implant 10, and the thread 20 into the transfer device 30 when using the dural sealing assembly of FIG. 1.

In an initial phase shown in FIG. 5a, that takes place during the manufacturing process, the introductory device 70, the implant 10, and the thread 20 are introduced into the transfer device 30. In addition, the stop 70b is housed in the notch 40 to avoid possible unwanted movements of the introductory device 70 before starting the operation of dural sealing.

Figure 5B:
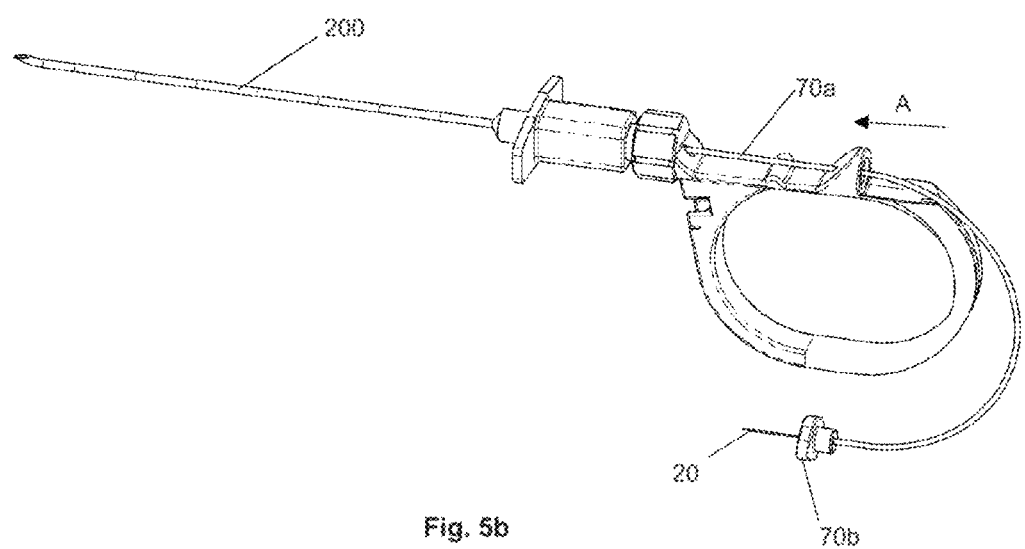
FIG. 5b illustrates the release of the stop 70b and the passage of the tube 70a through the nozzle 30c for introduction, together with the implant 10, and the guiding thread 20, inside the epidural needle 200 when using the dural sealing assembly of FIG. 1.

Subsequently, as shown in FIG. 5b, the stop 70b is released from the notch 40 and the tube is gently pressed, according to the direction indicated by the arrow A, in order for it to pass through the nozzle 30c and be introduced, together with the implant 10, and the guiding thread 20, inside the epidural needle 200.

Figure 5C:
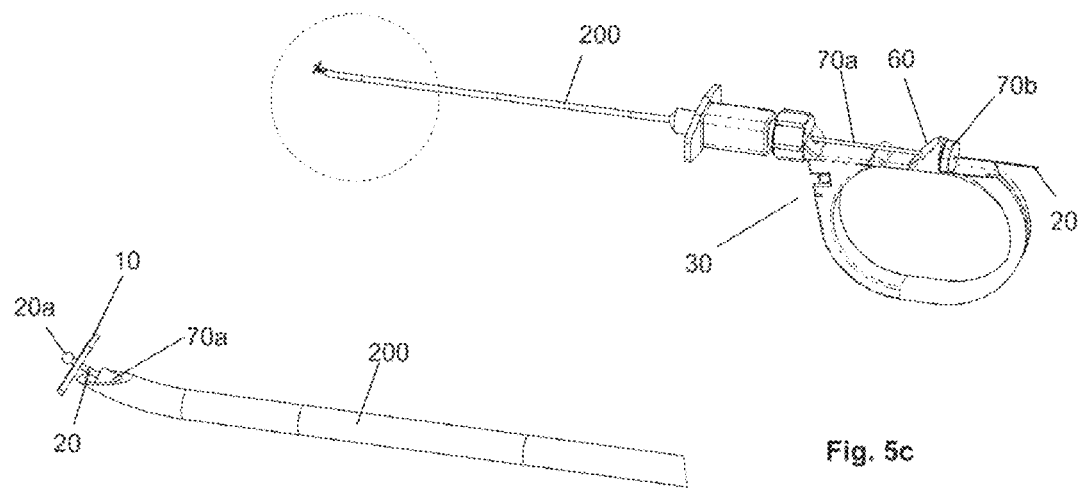
FIG. 5c illustrates how the implant 10 and the guiding thread 20 exit out of the tip of the needle 200 when using the dural sealing assembly of FIG. 1.
Figure 5D:
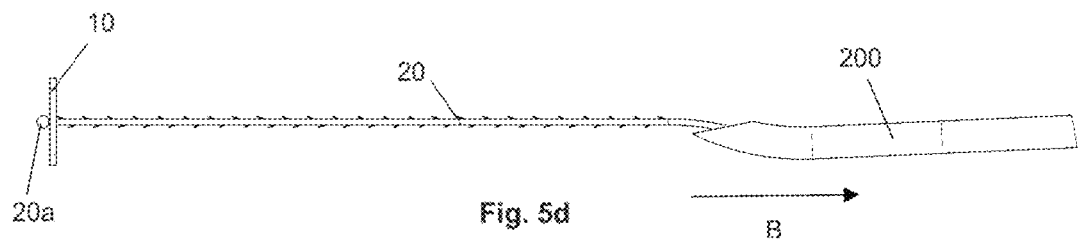
FIG. 5d illustrates the withdrawal of the assembly formed by the epidural needle 200, the transfer device 30, and the introductory device 70, once the implant 10 is fixed in position, when using the dural sealing assembly of FIG. 1.

At the end of this process, the tube 70a continues to be pushed until the stop 70b interferes with the block 60, as shown in FIG. 5c. In the magnified detail of said FIG. 5c, situated at the bottom left (which corresponds to the area enclosed by the dotted circle), it can be seen how the implant 10 and the guiding thread 20 finish by exiting out of the tip of the needle 200. Once the implant 10 is fixed in position, the assembly formed by the epidural needle 200, the transfer device 30, and the introductory device 70, are withdrawn according to the direction indicated by the arrow B, as shown in FIG. 5d.

Figure 6A:
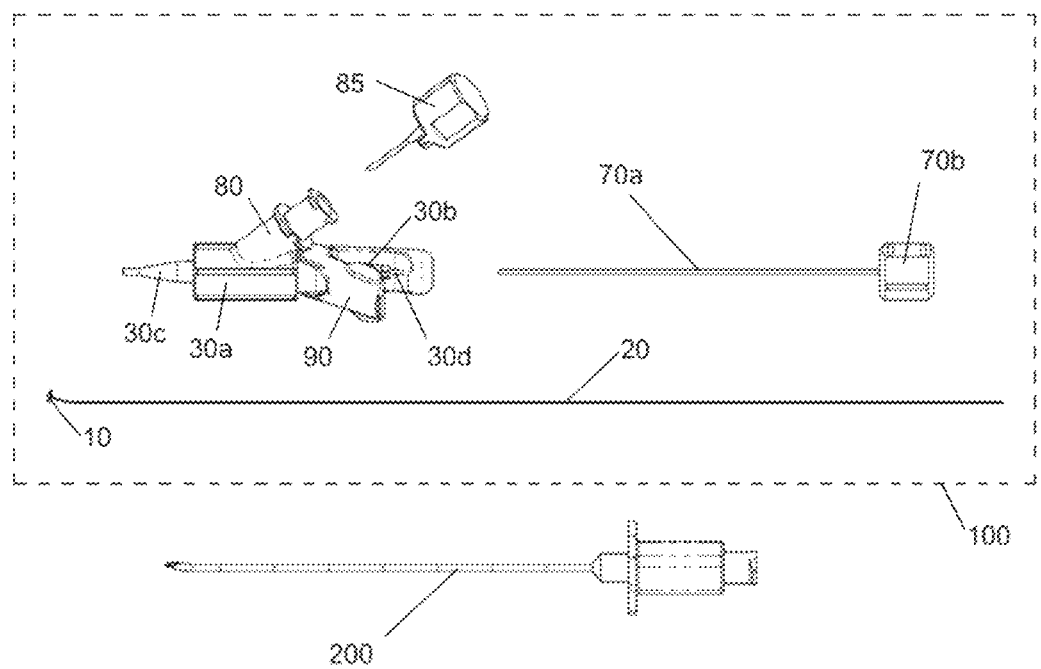
FIG. 6a shows the various elements that comprise a second embodiment of the dural sealing assembly according to the invention in schematic form.
Figure 6B:
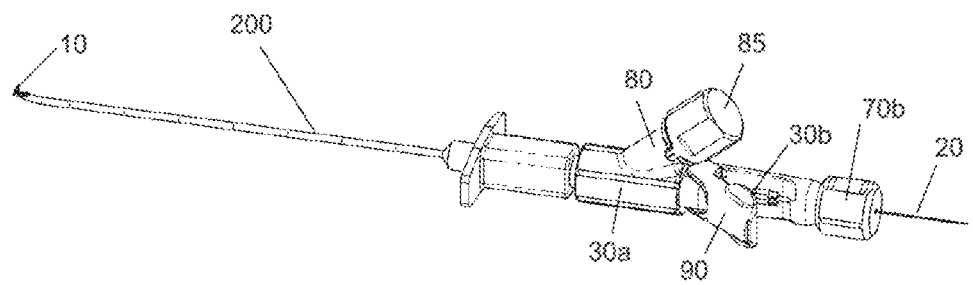
FIG. 6b shows a view of the dural sealing assembly of FIG. 6a with all its elements mounted.

FIGS. 6a and 6b show an alternative embodiment of the system 100 in which the transfer device 30 is provided with means 90 for blocking the introductory device 70. In this particular embodiment of the invention, the means 90 for blocking are a blocking tab.

In the embodiment shown in FIGS. 6a and 6b, the transfer device 30 is also provided with a conduit 80 for the administration of a surgical sealant, which can be closed by means of the plug 85.

LIST OF NUMERICAL REFERENCES USED IN THE FIGURES

(10) Implant;
(20) Guiding thread;
(20a) Widened portion, the end of the guiding thread;
(30) Transfer device;
(30a) The grip portion of the transfer device;
(30b) The portion of hollow longitudinal section of the transfer device;
(30c) Nozzle;
(30d) Entry region;
(35) Thread;
(40) Notch;
(50) Guiding projection;
(60) Block;
(70) Introductory device;
(70a) Tube of the introductory device;
(70b) Stop of the introductory device;
(80) Conduit for the administration of a surgical sealant;
(85) Plug;
(90) Blocking tab of the introductory device;
(100) The dural sealing system;
(200) Epidural needle;
(D1) Diameter of the guiding thread;
(D2) Diameter of the hollow section of the transfer device;
(D3) Internal diameter (lumen) of the epidural needle;
(D4) Internal diameter of the introductory device tube;

(D5) Total diameter of the introductory device tube;
(A) Direction of pushing the tube of the introductory device;
(B) Direction of withdrawal of the epidural needle, the transfer device, and the introductory device.

The invention claimed is:

1. A dural sealing system (100) comprising:
an implant (10) joined to a guiding thread (20) of diameter D1;
an introductory device (70) comprising a tube (70*a*) having an outside diameter D5, the tube (70*a*) having:
(i) an interior hollow section of diameter D4, wherein D4 is greater than D1,
(ii) a first free end, and
(iii) a second end having a stop (70*b*) positioned on said second end; and
a transfer device (30) comprising a grip portion (30*a*) and a nozzle (30*c*), wherein the nozzle comprises a first nozzle end (30*c*) and a second nozzle end (30*d*) with a hollow section (30*b*), of diameter D2, connecting the first and second nozzle ends, wherein the first nozzle end (30*c*) comprises an epidural needle coupling and the second nozzle end (30*d*) accommodates insertion of the tube (70*a*) of the introductory device (70) into the hollow section (30*b*), wherein the diameter of the hollow section (30*b*) is greater than the outside diameter D5 of the tube (70*a*), and wherein the grip portion comprises a notch (40) that accommodates the stop (70*b*) of the introductory device (70) when the tube (70*a*) is positioned in the hollow section (30*b*) of the nozzle (30*c*) and the first free end of the tube (70*a*) is positioned proximate to the first nozzle end (30*c*),
wherein the guiding thread (20) is co-axially positioned inside the interior hollow section of the tube (70*a*).

2. The dural sealing system (100) according to claim 1, wherein the transfer device further comprises a block positioned proximate to the second nozzle end (30*d*).

3. The dural sealing system (100) according to claim 1, wherein the implant (10) is positioned proximate to the first free end of the tube (70*a*).

4. The dural sealing system (100) according to claim 1, characterized in that the implant (10) is made of a biocompatible and bioreabsorbable material of synthetic or natural origin.

5. The dural sealing system (100) according to claim 4, characterized in that the implant (10) is made of polycaprolactone (PCL), polylactic acid (PLA), or combinations thereof.

6. The dural sealing system (100) according to claim 1, characterized in that the implant (10) has the shape of an elongated sheet with rounded ends, provided in its central portion with a hole to affix the guiding thread (20).

7. The dural sealing system (100) according to claim 1, characterized in that the guiding thread (20) is surgical suture thread provided with a widened end portion (20*a*).

8. The dural sealing system (100) according to claim 1, characterized in that the guiding thread (20) is barbed suture thread, with barbs set against the grain.

9. The dural sealing system (100) according to claim 1, wherein the epidural needle coupling comprises a threaded connection (35) for attaching an epidural needle (200) thereto.

10. The dural sealing system (100) according to claim 9, further comprising an epidural needle of internal diameter D3, wherein D3 is greater than D5.

11. The dural sealing system (100) according to claim 9, wherein the threaded connection (35) comprises a Luer-type threaded connection.

12. A method for sealing the dura mater of a patient previously subjected to a medical procedure which involved the puncture or perforation of the dura mater, comprising administering the implant (10) on the inner face of the dura mater, over said puncture or perforation, using the dural sealing system (100) according to claim 1.

13. The method according to claim 12, further comprising attaching the first nozzle end (30*c*) of said dural sealing system (100) to an epidural needle (200) prior to the administration of the implant (10).

14. The method according to claim 13, wherein said epidural needle (200) is that which caused said puncture or perforation of the dura mater and is not removed from said puncture or perforation of the dura mater prior to the administration of the implant (10).

15. A method of manufacturing the dural sealing system (100) according to claim 1 which comprises the following steps:
(a) introducing the first free end of the tube (70*a*) of the introductory device (70) into the second nozzle end (30*d*) until said first free end of said tube (70*a*) protrudes through the first nozzle end (30*c*);
(b) positioning the implant (10) proximate to said first free end of said tube (70*a*) with the thread (20) extending coaxially along the interior hollow section of said tube (70*a*), wherein said thread (20), to which said implant (10) is joined, is installed inside said introductory device (70) through said first free end of said tube (70*a*);
(c) positioning said implant (10) and the first free end of the tube (70*a*) within, and proximate to, the first nozzle end of the nozzle (30*c*) by jointly moving said introductory device (70) with said implant (10) situated proximate to said first free end of said tube (70*a*) and the thread (20) extending coaxially along the hollow section of the tube into the transfer device through said first nozzle end (30*c*).

* * * * *